US012575955B2

(12) United States Patent (10) Patent No.: US 12,575,955 B2

Tang (45) Date of Patent: Mar. 17, 2026

(54) DEVICE FOR CONTROLLING CURVE ANGLE OF SCOLIOSIS

(71) Applicant: Tsz Hin Tang, Hong Kong (CN)

(72) Inventor: Tsz Hin Tang, Hong Kong (CN)

( * ) Notice: Subject to any disclaimer, the term of this patent is extended or adjusted under 35 U.S.C. 154(b) by 426 days.

(21) Appl. No.: 18/475,992

(22) Filed: Sep. 27, 2023

(65) Prior Publication Data

US 2024/0041631 A1 Feb. 8, 2024

(30) Foreign Application Priority Data

Aug. 5, 2022 (CN) .......................... 202210938550.2

(51) Int. Cl.
*A61F 5/02* (2006.01)

(52) U.S. Cl.
CPC .............. *A61F 5/026* (2013.01); *A61F 5/024* (2013.01)

(58) Field of Classification Search
CPC .. A61F 5/02–03; A61F 5/24–37; A63B 21/06; A63B 21/065; A63B 21/4001; A63B 21/4007; A63B 26/00; A63B 26/003; A63B 2026/006
See application file for complete search history.

(56) References Cited

U.S. PATENT DOCUMENTS

| | | | | |
|---|---|---|---|---|
| 5,067,484 A | * | 11/1991 | Hiemstra-Paez ....... | A61F 5/026 |
| | | | | 602/19 |
| 5,211,163 A | * | 5/1993 | Mortenson ............. | G01G 19/44 |
| | | | | 600/592 |
| 5,547,445 A | * | 8/1996 | Chang .................. | A63B 21/065 |
| | | | | 482/93 |
| 5,768,706 A | * | 6/1998 | Griffith ................ | A63B 21/065 |
| | | | | 2/102 |
| 8,900,146 B2 | | 12/2014 | Zheng et al. | |
| 9,535,168 B2 | | 1/2017 | Desaute | |
| 11,497,433 B2 | * | 11/2022 | An ....................... | A61B 5/1101 |
| 2007/0049854 A1 | | 3/2007 | Teimourian | |
| 2011/0043755 A1 | * | 2/2011 | Gibson-Horn .......... | A61F 5/028 |
| | | | | 351/203 |

FOREIGN PATENT DOCUMENTS

| | | |
|---|---|---|
| CN | 209951489 U | 1/2020 |
| CN | 113303959 A | 8/2021 |
| CN | 218552529 U | 3/2023 |

(Continued)

OTHER PUBLICATIONS

"Technical Guidelines for Prevention and Control of Spinal Curvature Abnormalities in Children and Adolescents", dated Nov. 1, 2021, 14 pages.

(Continued)

*Primary Examiner* — Michelle J Lee

(74) *Attorney, Agent, or Firm* — Quarles & Brady LLP

(57) ABSTRACT

The present disclosure provides a device for controlling one or more curve angles of scoliosis. The device includes a holding module and a weight module. The holding module is configured to be worn on the front-of-chest position of a user, and the holding module is provided with weight-hanging site. The weight module is suspended naturally on the weight-hanging site, and a weight-load of the weight module unit is configured to keep one or more curve angles of scoliosis of the user within a pre-defined range.

11 Claims, 12 Drawing Sheets

(56) References Cited

FOREIGN PATENT DOCUMENTS

| JP | 2008149174 A | 7/2008 |
| KR | 20170042163 A | 4/2017 |
| WO | 2018105760 A1 | 6/2018 |

OTHER PUBLICATIONS

Research Progress of Brace and Conservative Treatment of Adolescent Idiopathic Scoliosis, Wenlei Wang et al., dated Nov. 29, 2021, 9 pages.

Brace Treatment in Adolescent Idiopathic Scoliosis: Risk Factors for Failure—a Literature Review, The Spinal Journal, Ron El Hawary, MD et al., dated Jul. 15, 2019, 9 pages.

2016 SOSORT guidelines: orthopedic and rehabilitation treatment of idiopathic scoliosis during growth, Stefano Negrini et al., 48 pages.

The Classification of Scoliosis Braces Developed by SOSORT with SRS, ISPO, and POSNA and Approved by ESPRM, Stefano Negrini et al., 10 pages.

Biomechanical characteristics and therapy strategy of idiopathic scoliosis: research advance, Yi-ming Zou et al., 5 pages.

Cheng, Jack C et al. "Adolescent Idiopathic Scoliosis." Nature Reviews—Disease Primer, dated Oct. 15, 2015, 21 pages.

Weinstein, Stuart L. et al. "Adolescent Idiopathic Scoliosis." The Lancet, vol. 371, dated May 3, 2008, 11 pages.

Effects of Bracing in Adolescents with Idiopathic Scoliosis, Stuart L. Weinstein et al., New England Journal of Medicine, dated Sep. 19, 2013, 10 pages.

The Effect of Rigid versus Flexible Spinal Orthosis on the Clinical Efficacy and Acceptance of the Patients with Adolescent Idiopathic Scoliosis, Man Sang Wong PhD et al., Spine, vol. 33, dated 2008, 6 pages.

Office Action, corresponding to SG11202503732U, dated Sep. 12, 2025.

International Search Report, corresponding to PCT/CN2023/122314, dated Dec. 20, 2023.

* cited by examiner

140

140

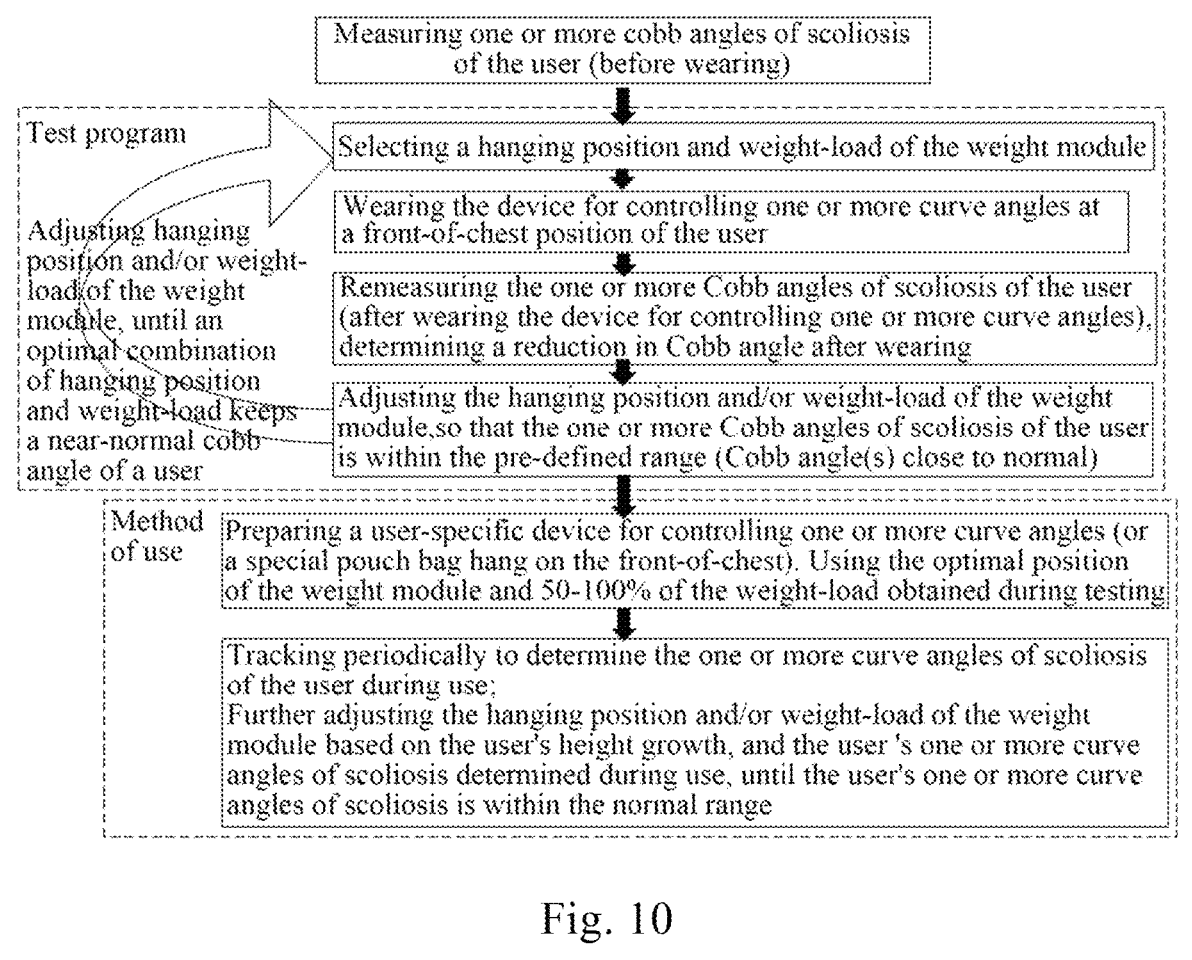

Measuring one or more cobb angles of scoliosis
of the user (before wearing)

Test program

Selecting a hanging position and weight-load of the weight module

Adjusting hanging
position and/or weight-
load of the weight
module, until an
optimal combination
of hanging position
and weight-load keeps
a near-normal cobb
angle of a user Wearing the device for controlling one or more curve angles at
a front-of-chest position of the user Remeasuring the one or more Cobb angles of scoliosis of the user
(after wearing the device for controlling one or more curve angles),
determining a reduction in Cobb angle after wearing Adjusting the hanging position and/or weight-load of the weight
module,so that the one or more Cobb angles of scoliosis of the user
is within the pre-defined range (Cobb angle(s) close to normal)

Method
of use

Preparing a user-specific device for controlling one or more curve angles (or
a special pouch bag hang on the front-of-chest). Using the optimal position
of the weight module and 50-100% of the weight-load obtained during testing Tracking periodically to determine the one or more curve angles of scoliosis
of the user during use;
Further adjusting the hanging position and/or weight-load of the weight
module based on the user's height growth, and the user 's one or more curve
angles of scoliosis determined during use, until the user's one or more curve
angles of scoliosis is within the normal range

Fig. 10

Cobb
angle (B)Indicating a
significant reduction
in Cobb angle by
repeated low-dose
X-ray testing after
use of the device for
controlling one or
more curve angles
of scoliosis by front-
of-chest weight-
bearing (7.5kg)

(A)Natural Cobb angle
without weight-bearing

DEVICE FOR CONTROLLING CURVE ANGLE OF SCOLIOSIS

CROSS-REFERENCE TO RELATED APPLICATIONS

This patent application claims the priority from Chinese Patent Application No. 202210938550.2, filed on Aug. 5, 2022 and entitled "Device for Controlling Curve Angle of Scoliosis," the entire disclosure of which is hereby incorporated by reference.

TECHNICAL FIELD

The present disclosure relates to the technical field of an orthosis device, in particular, to a device for controlling one or more curve angles of scoliosis.

BACKGROUND

The most common type of abnormal spinal curvature in children and adolescents is idiopathic scoliosis (Weinstein et al. 2008; Cheng et al. 2015).

Scoliosis is a three-dimensional structural deformity of the spine in which multiple vertebrae of the spine deviate from a midline of the body to form a curvature. In many cases, there is additional rotation and kyphosis or lordosis curvature of the vertebral body. The diagnosis of scoliosis is based on the Cobb angle, which is measured using a standard standing full spine "X"-ray film. A Cobb angle of $\geq 10°$ is usually defined as scoliosis.

According to the etiology, scoliosis is commonly categorized into Adolescent Idiopathic Scoliosis (AIS) and other types. Adolescent idiopathic scoliosis is predominantly found in adolescent females and is the most common type occurring in children and adolescents, and its etiology is unknown. Genetic and environmental factors have been reported to play a role in the development of adolescent idiopathic scoliosis.

Currently, non-surgical treatments for scoliosis focus on screening, correcting standing and sitting postures, and proper use of backpacks to equalize the weight on both shoulders carrying the backpacks.

Besides, a non-surgical option to correct scoliosis is the use of a brace (Negrini et al. 2022; 2018). There are various types of braces, which may be broadly categorized into rigid and soft (Wong et al. 2008), and rigid brace includes the Boston brace. An example of a soft brace is the SpineCor, while a soft brace uses elastic rubber bands to pull the curvature of the spine. However, the efficacy of brace in the treatment of scoliosis remains inconclusive (Weinstein et al. 2013). In recent years, studies have analyzed and synthesized various factors that influence the effectiveness of braces on scoliosis (Hawary et al. 2019).

Rigid scoliosis braces are generally made of hard and rigid materials, but more recently there have been a number of scoliosis braces made of elastic materials to create tension (U.S. Pat. No. 8,795,213B2, Spinal Orthosis). All of these existing braces have one thing in common: they all have a portion of the brace fixed to the hip or lumbar spine (e.g., U.S. Pat. No. 9,220,625B2 Thoracic lumbar sacral orthosis) for attachment of other brace portions for purposes of correcting the curvature. The biomechanics principle of all these braces to correct scoliosis is through the use of the pelvis as a fixation point below, in other words, these braces achieve correction by such generated correction force, which may not only adversely affects bodies of children and adolescents, but also has a bad user experience.

SUMMARY

The present disclosure provides a device for controlling one or more curve angles of scoliosis that can at least partially solve the above problems of the technology of currently available devices.

In one aspect, the present disclosure provides a device for controlling one or more curve angles of scoliosis, which includes: a holding module to be worn in front of the chest of a user, the holding module having a weight-hanging site; and a weight module suspended on the weight-hanging site, the weight-load of the weight module unit being configured to keep one or more curve angles of scoliosis of the user within a pre-defined range.

In some embodiments, the weight-hanging site is configured to allow selection among a plurality of different hanging positions to suspend the weight module thereon; and when the weight-hanging site is at different suspension positions, a weight-load of the weight module suspended on the weight-hanging site keeps the one or more curve angles of scoliosis of the user within the pre-defined range and identifies the optimal position.

In some embodiments, the holding module is provided with a horizontal slot; the weight-hanging site is provided inside the horizontal slot, and the weight-hanging site is configured to slide within the horizontal slot to move between the plurality of various suspension positions to find the optimum position of the weight.

In some embodiments, the holding module is provided with a plurality of the weight-hanging sites, the plurality of the weight-hanging sites are located at different suspension positions; and when a plurality of the weight-hanging sites in different combinations suspend the weight module, a combination of the weights of the weight module keeps the one or more curve angles of scoliosis of the user within the pre-defined range.

In some embodiments, a plurality of the weight-hanging sites in different combinations are located on the same horizontal line.

In some embodiments, the holding module is provided with a horizontal slot; the plurality of the weight-hanging sites are provided in the horizontal slot, and the plurality of the weight-hanging sites are configured to slide within the horizontal slot to be located at different suspension positions.

In some embodiments, the device further includes shoulder straps, connected to the holding module, used to position the holding module at the front-of-chest position of the user when worn on the shoulders of the user; and a pressure pad, provided on a back connecting strap between shoulder straps, located at a back position opposite to the front-of-chest position, where the pressure pad is configured to push thoracic vertebrae forward from the back.

In some embodiments, the device further includes a pouch bag, the pouch bag having a storage space; where the holding module and the weight module are configured together with the storage space of the pouch bag, and the shoulder straps is connected to the pouch bag.

In some embodiments, the holding module, the weight-hanging site and the weight module are made of a material transparent to X-rays.

In another aspect, the present disclosure provides a device for controlling one or more curve angles of scoliosis, including: a front chest bag, the front chest bag is configured to be worn at the front-of-chest position of a user; and a weight-bearing module, fixedly disposed in the pouch, the weight-bearing module being configured to carry the weight of articles carried inside the front chest bag and a weight of the carried articles being configured to keep a curvature of scoliosis of the user within a pre-defined range.

In some embodiments, the weight-bearing module includes: a connecting frame, the connecting frame extending in a direction of gravity, configured to be fixedly connected to one side of an interior of the front chest bag that is close to the front-of-chest position of the user; and a articles-bearing platform, connected to the connecting frame, and the articles-bearing platform extending in a horizontal direction.

In some embodiments, the front chest bag, the weight-bearing module and the carried article are made of a material transparent to X-rays. The weight-bearing module may alternatively be suspended outside the range irradiated by the X-ray.

In some embodiments, the front chest bag includes a body pouch and shoulder straps; the device for controlling one or more curve angles of scoliosis further includes a pressure pad; where, the pressure pad is provided on a back connecting strap between shoulder straps, located at a back position opposite to the front-of-chest position, and the pressure pad is configured to push thoracic vertebrae forward from the back.

In another aspect, the present disclosure provides a method for using the device for controlling one or more curve angles of scoliosis, including: determining one or more curve angles of scoliosis of a user; determining a weight-load for the weight module that keeps the one or more curve angles of scoliosis of the user within a pre-defined range; wearing the device for controlling one or more curve angles of scoliosis at a front-of-chest position of the user; re-determining one or more curve angles of scoliosis of the user after wearing the device for controlling one or more curve angles of scoliosis; and adjusting a hanging position and/or the weight-load of the weight module to keep the one or more curve angles of scoliosis of the user within the pre-defined range.

In some embodiments, the method further includes: tracking periodically to determine the one or more curve angles of scoliosis of the user during use; and adjusting the hanging position and/or the weight-load of the weight module based on the one or more curve angles of scoliosis of the user determined during use, until the one or more curve angles of scoliosis of the user is within the pre-defined range or close to a normal range.

In some embodiments, the duration of using the device for controlling one or more curve angles of scoliosis may vary from person to person and to suit the needs and comfort, and convenience of a user, e.g., time to go to class and time to leave class or several hours per day.

The device for controlling one or more curve angles of scoliosis provided by at least one embodiment of the present disclosure is worn at the front-of-chest position of the user, so that the weight module unit is suspended naturally on the holding module, thus the gravitation force of the weight module is applied to reduce the one or more curve angles of scoliosis of the user. The above device for controlling one or more curve angles of scoliosis is simple in structure, easy to implement, and does not exert force or interact with other parts of the user's body, i.e., it does not affect other body parts of the user.

BRIEF DESCRIPTION OF THE DRAWINGS

Other features, objectives, and advantages of the present disclosure will become more apparent, by reading detailed descriptions of non-limiting embodiments with reference to the following accompanying drawings.

FIG. 10 is a flow diagram of a method for using a device for controlling one or more curve angles of scoliosis according to an embodiment of the present disclosure.

DETAILED DESCRIPTION OF EMBODIMENTS

Figure 1A:
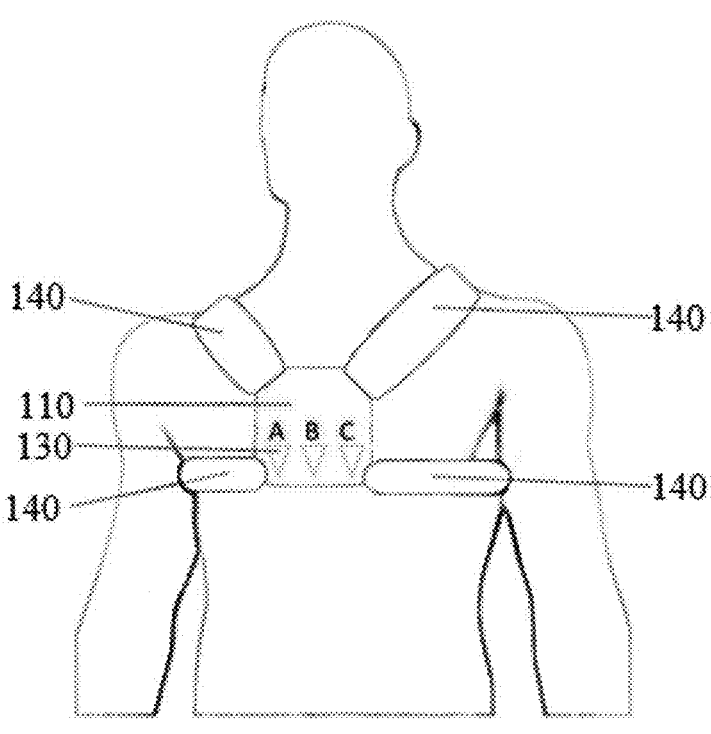
FIG. 1A and FIG. 1B are front views of a user wearing a device for controlling one or more curve angles of scoliosis without suspending a weight module unit, and after suspending the weight module unit, respectively according to a first embodiment of the present disclosure.

To better understand the present disclosure, aspects of the present disclosure will be described in more detail with reference to the accompanying drawings. It should be understood that these detailed descriptions are merely descriptions of sample embodiments of the present disclosure and are not intended to limit the scope of the present disclosure in any way. Throughout the specification, the same reference numerals refer to the same components. The expressions "and/or" include any and all combinations of one or more of the listed items in association.

In the accompanying drawings, the thicknesses, sizes, and shapes of the components have been slightly adjusted for ease of description. The accompanying drawings are for illustrative purposes only and are not strictly drawn to scale. As used herein, the terms "roughly," "approximately," and the like are used as terms of approximation, and are intended to account for inherent deviations in measured or calculated values that would be recognized by those of ordinary skill in the field.

It should be further understood that the expressions such as "comprise," "comprising," "having," "include" and/or "including," when used in this specification, are open-ended rather than closed-ended, these words specify the presence of stated features and components, but do not exclude the presence of one or more other features, elements, components and/or combinations thereof. In addition, expressions such as "at least one of," when preceding a list of listed features, modify the entire list of features rather than an individual element in the list. In addition, when describing embodiments of the present disclosure, the use of "may" indicates "one or more embodiments of the present disclosure". Furthermore, the term "as an example" is intended to refer to examples or illustrations.

Unless otherwise defined, all terms (including engineering terms and scientific terms) used herein have the same meaning as commonly understood by those of ordinary skill in the field to which the present disclosure belongs. It should be further understood that unless expressly stated in the present disclosure, words defined in commonly used dictionaries should be construed as having a meaning consistent with their meaning in the context of the prior art and should not be construed in an idealized or overly formalized sense.

It should be noted that the embodiments and features in the embodiments in the present disclosure may be combined with each other on a non-exclusive basis. In addition, unless expressly limited or contradicted by the context, the specific steps included in the methods described in the present disclosure need not be limited to the sequence described, but may be performed in any sequence or simultaneously. The present disclosure will be described in detail below with reference to the accompanying drawings and in conjunction with the embodiments.

In addition, the use of "connection" or "coupling" in the present disclosure may indicate direct contact or indirect contact between the corresponding components, unless expressly otherwise limited or capable of being deduced from the context.

An embodiment of the present disclosure provides a device for controlling curve angle of scoliosis, including a holding module and a weight module. The holding module is configured to be worn at the front-of-chest position of a user, and the holding module is provided with a weight-hanging site. The weight module is suspended on the weight-hanging site, and the weight-load of the weight module unit is configured to keep one or more curve angles of scoliosis of the user within a pre-defined range. In the above scheme, the weight module is suspended naturally on the holding module, so that a gravitational force on the weight module acts to reduce the one or more curve angles of scoliosis of the user. The above device for controlling one or more curve angles of scoliosis is simple in structure, easy to implement, and does not interact with other parts of the user's body during use, i.e., it does not affect other body parts of the user.

The device for controlling one or more curve angles of scoliosis in the present disclosure is very different from conventional scoliosis braces. The present disclosure uses the gravitational force of the weight module to reduce the one or more curve angles of scoliosis of the user. The present disclosure is simple in structure, easy to wear, and acceptable to adolescents.

Furthermore, the applicable range of current available scoliosis brace orthosis only covers from 20° to 40°, so there is no orthosis device suitable to correct scoliosis of low curve angles (Cobb<20). The present disclosure is suitable for use in this range 10<Cobb<20, to help child patients with early-stage scoliosis. Imaging showed an improvement in one or more curve angles of scoliosis after wearing this device of the present disclosure for controlling one or more curve angles of scoliosis.

An Embodiment of the Present Disclosure Will be Described in Detail Below in Conjunction with FIG. 1 to FIG. 5.

In an embodiment shown in FIG. 1A and FIG. 1B, FIG. 2, and FIG. 3A, a device 100 for controlling one or more curve angles of scoliosis includes a holding module 110 and a weight module 120. The holding module 110 is configured to be worn at a front-of-chest position of a user, the holding module 110 is provided with a weight-hanging site 130, and the weight-hanging site 130 is configured to allow the weight module to be suspended at different positions. When the weight-hanging site 130 at different suspension positions is suspended with the weight module 120, the weight-load of the weight module 120 is configured to keep one or more curve angles of scoliosis of the user within a pre-defined range, which is closer to a normal angle.

Since the curvature and structure of the scoliotic spine is different for different individuals, it is necessary to adjust the center of gravity of the weight module unit 120 at the front-of-chest position for different users. In the above scheme, the position and/or the weight-load of the weight module 120 suspended naturally on the holding module 110 may be adjusted, so that device 100 for controlling one or more curve angles of scoliosis can tune the most suitable hanging position and weight for each of the different users, so that the one or more curve angles of scoliosis of the user may be reduced and close to a normal angle.

Figure 1B:
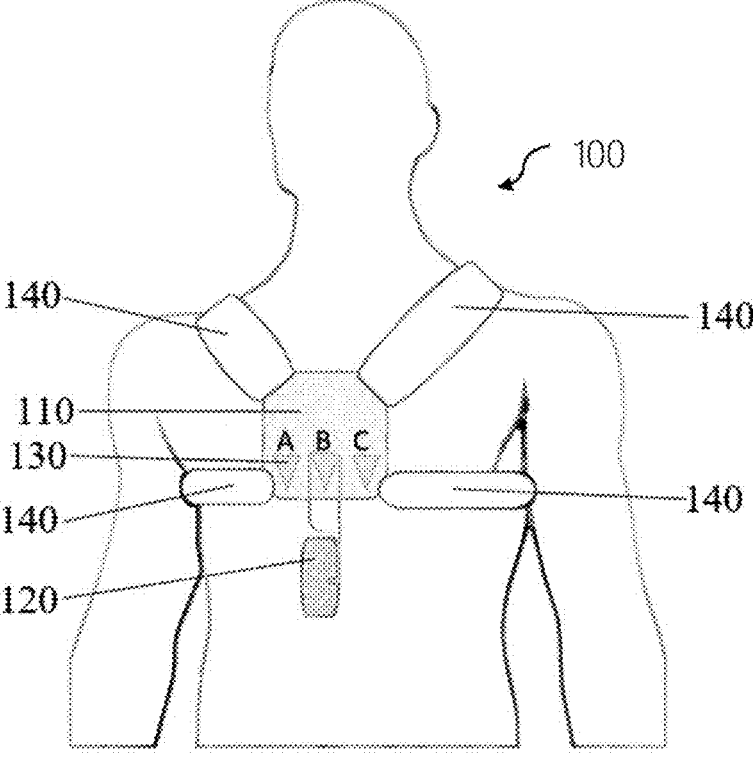
Figure 2:
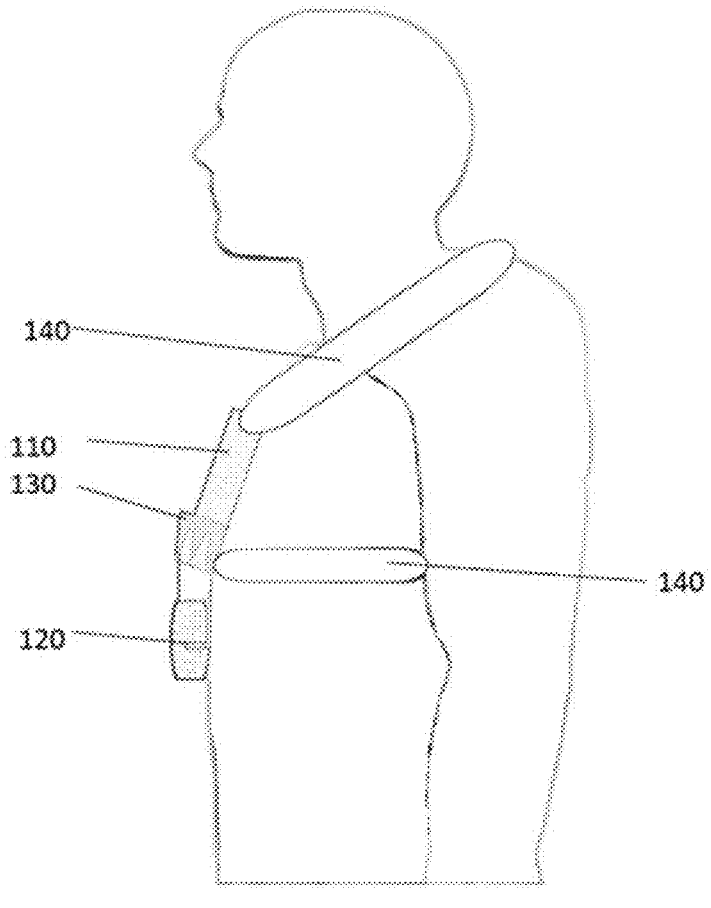
FIG. 2 is a side view of a user after wearing the device for controlling one or more curve angles of scoliosis according to the first embodiment of the present disclosure.

As an example, as shown in FIG. 1B, the position of the weight-hanging site 130 may be in mid-front of the user's body (with reference to the B position in the figure), in left-front (with reference to the C position in the figure) or in right-front (with reference to the A position in the figure). Moreover, the weight-load of the weight module 120 at each position may also be adjusted to suit different users, so that the one or more curve angles of scoliosis of the user may be reduced, to be closer to a normal angle.

It should be noted that the determination of position of the weight-hanging site 130 and the weight-load of the weight module 120 is based on the position at which each user can obtain the largest correction effect by wearing the device for controlling one or more curve angles of scoliosis in the present disclosure.

Alternatively, comparisons can be made by repeated spinal imaging or low-dose spinal X-ray film (EOS, EOS-imaging.com, Radiographic imaging device and detector for a radiographic imaging device, U.S. Pat. No. 9,535,168B2) or ultrasound (Three-dimensional ultrasound imaging system for assessment of Scoliosis, U.S. Pat. No. 8,900,146B2) testing, to find an optimal configuration of the hanging position of the weight-hanging site 130 and the weight-load of the weight module 120.

In addition, the weight-load of the weight module 120 is approximately between 5 kg and 10 kg, thus, the holding module 110 as well as the weight-hanging site 130 should have a certain strength and should at least be able to withstand the weight-load of the weight module 120.

Figure 4:
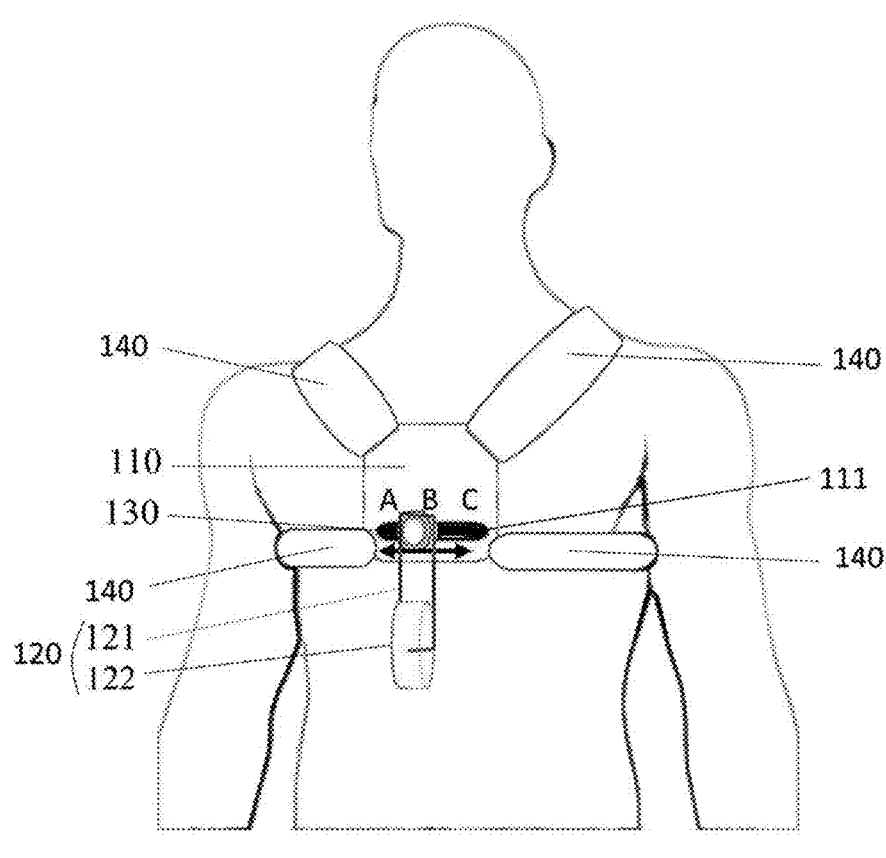
FIG. 4 is a schematic structural diagram of another implementation example of the device for controlling one or more curve angles of scoliosis according to the first embodiment of the present disclosure, where a horizontal slot is provided on which the position of the weight module can move horizontally.

In some embodiments, as shown in FIG. 4, the weight module 120 may include a cord 121 and a weight 122. Preferably, the weight 122 is suspended on the weight-hanging site 130 by the cord 121.

In some embodiments, the adjustment the level of center of gravity of the weight 122 may also be achieved by adjusting the length of the cord 121.

In some embodiments, the holding module 110 is provided with a horizontal slot 111, the weight-hanging site 130 is provided in the horizontal slot 111, and the weight-hanging site 130 is configured to slide within the horizontal slot 111 to move between the plurality of different suspension positions.

In the above scheme, by using the horizontal slot 111, the weight-hanging site 130 may simply and easily move between the different suspension positions, thereby achieving the purpose of adjusting the center of gravity of the weight module 120. This embodiment facilitates the tuning of the position of the weight-hanging site, and is used when tuning for the most suitable hanging position and weight for an individual user, then spinal imaging is repeated to obtain the one or more curve angles of scoliosis when the weight module is suspended at different positions and of different weights. It is then possible to find out which configuration can reduce the one or more curve angles of scoliosis of the user and make the one or more curve angles of scoliosis of the user close to a normal angle.

In some embodiments, the holding module 110 further includes a restricting portion (not shown), and the restricting portion is used to fasten the weight-hanging site 130 after the position of the weight-hanging site 130 has been determined, preventing the weight-hanging site 130 from shifting thereby resulting in loss or reduction of correction effects.

Alternatively, a number of restricting slots (not shown) are provided at a lower edge of the horizontal slot 111, and the weight-hanging site 130 may be embedded in the restricting slots, thereby preventing the weight-hanging site 130 from shifting.

The weight-hanging site 130 in the above embodiment may be in the form of a hook, a hanging rod, etc., or other forms capable of realizing the above function, which is not limited in the present disclosure.

Figure 5:
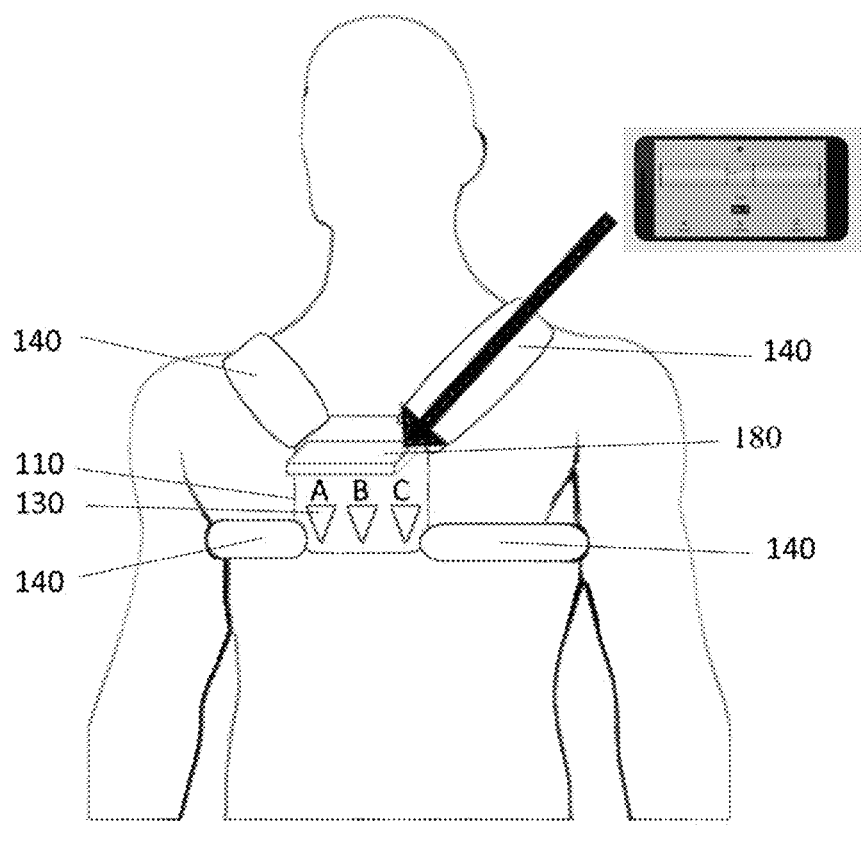
FIG. 5 is another schematic structural diagram of the device for controlling one or more curve angles according to the first embodiment of the present disclosure.

In some embodiments, as shown in FIG. 5, the holding module 110 may also be provided with a platform 180. The platform is configured to place a device such as a gradient meter or a smartphone to thereby determine whether the horizontal slot 111 is at a horizontal position after the holding module 110 has been worn at the front-of-chest position of the user.

Alternatively, the platform and the holding module 110 are in the form of a removable or collapsible connection.

In some embodiments, the device 100 for controlling one or more curve angles of scoliosis further includes shoulder straps 140 and a pressure pad. The shoulder straps 140 are connected to the holding module 110, used to position the holding module 110 at the front-of-chest position of the user when worn on the shoulders of the user. The pressure pad is provided on a back connecting strap between the shoulder straps 140, located at a back position opposite the front-of-chest position, and the pressure pad is configured to push vertebrae forward from the back. The shoulder straps 140 in the above scheme may be provided with one or two straps.

In some embodiments, one shoulder strap 140 can be set diagonally across one shoulder and back of the user, and then extends out from below the axilla of the other side to be connected to the holding module 110 at the front-of-chest position, so as to achieve the purpose of fixing the holding module 110 at the front-of-chest position of the user. In this regard, the pressure pad is placed between the shoulder strap 140 and the back of the user, presses the vertebrae forward from the back the user under the action of the shoulder strap 140, and increases a force of pushing the vertebrae forward, which is helpful in controlling the one or more curve angles of scoliosis of the user.

In some embodiments, the shoulder straps 140 include two shoulder straps 140 and one back connecting strap 150.

Figure 3A:
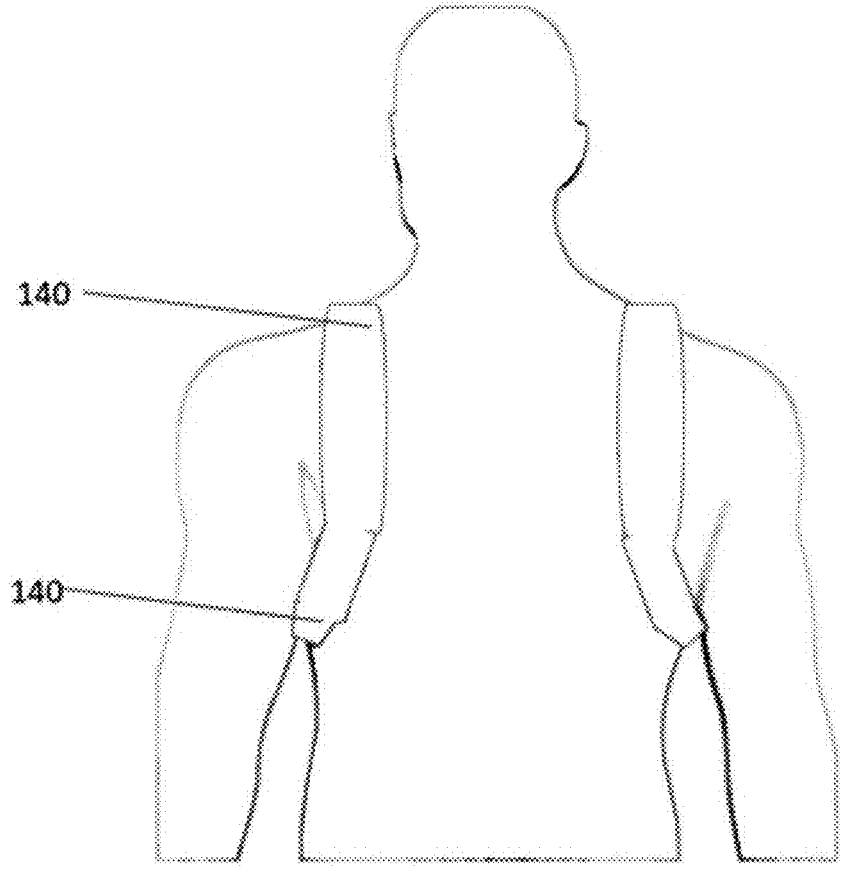
FIG. 3A and FIG. 3B are rear views of a user after wearing the device for controlling one or more curve angles of scoliosis according to the first embodiment of the present disclosure, respectively.
Figure 3B:
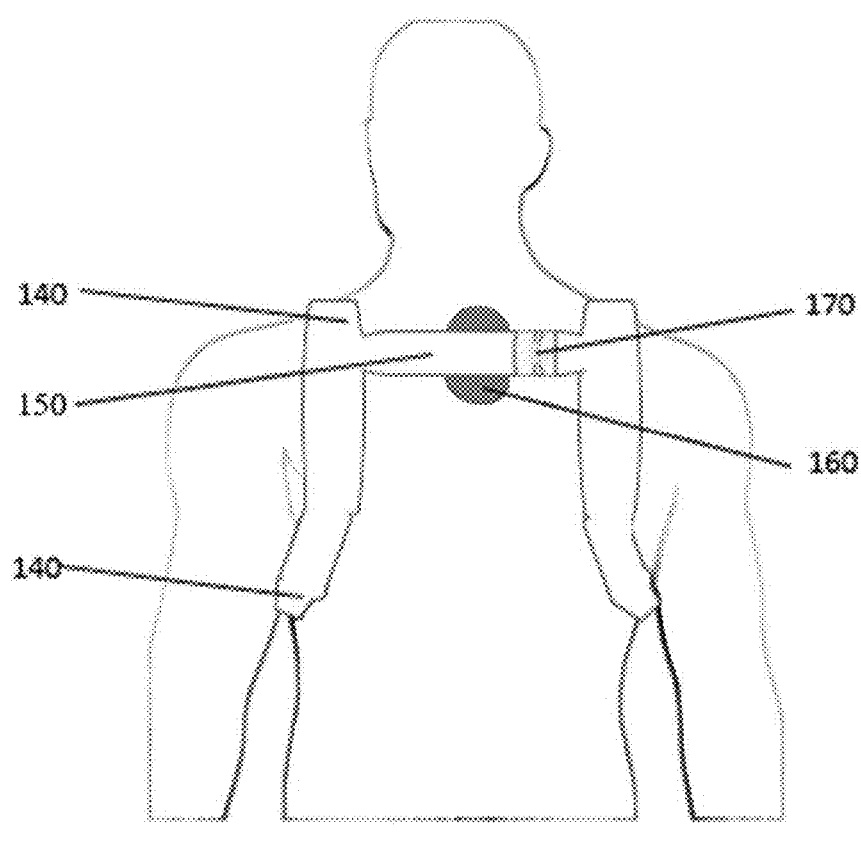

The two side shoulder straps 140 may wrap around the shoulders on both sides of the user and the back, and then extend out from below the axillas to be connected to the holding module 110 at the front-of-chest position, to achieve the purpose of fixing the holding module 110 at the front-of-chest position of the user. The back connecting strap 150 connects the two shoulder straps 140, and is located at a back position of the user. The back connecting strap 150 may be made of a highly elastic material, and thus the back connecting strap 150 constitutes of the pressure pad, as shown in FIG. 3B. When worn, the back connecting strap 150 is positioned at a high vertebrae (e.g., T1 to T6), and above the apex vertebra corresponding to the apex of the lateral eminence of the scoliosis. The highly elastic back connecting strap 150 may also have a pressure pad 160 placed at a position in close proximity to the vertebrae, so that a pressure provided by the back connecting strap 150 is evenly distributed across the vertebrae to readjust the vertebrae at the back position of the user and increase the force of pushing the vertebrae forward.

In addition, the shoulder straps 140 may be provided in a decompressed state to prevent the shoulder straps 140 from making the shoulders of the user uncomfortable under the weight-load of the weight module 120.

In some embodiments, the back connecting strap 150 may further be equipped with a simple buckle 170 that facilitates opening and locking the back connecting strap 150.

In some embodiments, the device 100 for controlling one or more curve angles of scoliosis further includes a pouch bag (e.g., FIG. 8) that hangs in front of the body and has a capacity space. The holding module 110 and the weight module 120 are provided in the capacity space of the pouch bag, and the shoulder straps 140 is connected to the pouch bag.

In the above scheme, by configuring a pouch bag for the device 100 for controlling one or more curve angles of scoliosis, on the one hand, the aesthetics of the device 100 for controlling one or more curve angles of scoliosis is improved, on the other hand, it is also convenient for the user to wear, which improves the user's experience of using the device 100 for controlling one or more curve angles of scoliosis in the present disclosure.

In some embodiments, various components (the holding module 110, the weight-hanging site 130, and the weight module 120, the pouch bag, the shoulder straps 140, or the like) of the device 100 are made of a material transparent to X-rays, so as to facilitate the determination of the one or more curve angles of scoliosis by means of X-ray imaging again after the apparatus has been worn. As an example, a material of plastic is used.

An Embodiment of the Present Disclosure Will be Described in Detail Below in Conjunction with FIG. 6 and FIG. 7.

Figure 6:
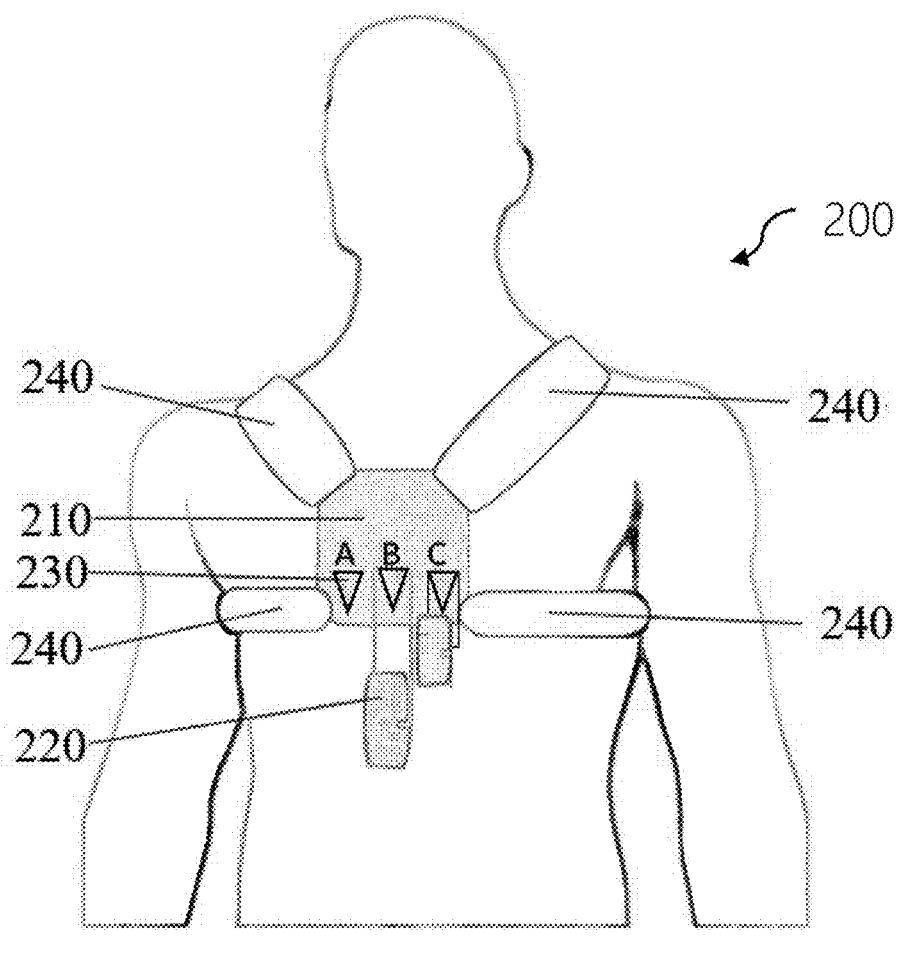
FIG. 6 is a front view of a user after wearing a device for controlling one or more curve angles of scoliosis according to a second embodiment of the present disclosure.

In the embodiment as shown in FIG. 6, a device 200 for controlling one or more curve angles of scoliosis includes a holding module 210 and a weight module 220. The holding module 210 is configured to be worn at a front-of-chest position of a user, and the holding module 210 is provided with a weight-hanging site 230. The weight-hanging site 230 is provided to suspend the weight module 220 thereon.

Unlike the previous embodiments, the holding module 210 in the present embodiment is provided with multiple weight-hanging sites 230, and many of the weight-hanging sites 230 are located at different suspension positions. Multiple weight-hanging sites 230 in different locations suspend the weight module, and the weight-load of the weight module 220 is configured to keep the one or more curve angles of scoliosis of the user within a pre-defined range.

In the above scheme, the device 200 for controlling one or more curve angles of scoliosis can be adapted to fit the majority of users with scoliosis by adjusting the position and/or the weight and/or the number of the weight module 220 suspended naturally on the holding module 210. Moreover, it may also be possible to enable the device 200 for controlling one or more curve angles of scoliosis to be adapted to the one or more curve angles of scoliosis of the same user at different stages of correction.

As an example, in FIG. 6, the weight-hanging site 230 may be positioned to suspend the weight module 220 and the weight-load of the weight module 220 in any combination of in mid-front of the user's body (with reference to B in the figure), to left-front (with reference to C in the figure) or to the right-front (with reference to A in the figure).

It should be noted that the number and position of the weight-hanging sites 230 and the weight-load of the weight module 220 depend on the positions at which each user can obtain the maximum spinal curvature correction effect by wearing the device for controlling one or more curve angles of scoliosis in the present disclosure.

Alternatively, comparisons can be made by repeated spinal imaging or spinal X-ray film or ultrasound testing to find the optimal configuration of the number of weight-hanging sites 230, the hanging position, and the weight-load of the weight module 220 to minimize the one or more curve angles of scoliosis of the user.

In some embodiments, multiple of the weight-hanging sites 230 in different configurations are located on the same horizontal line.

Figure 7:
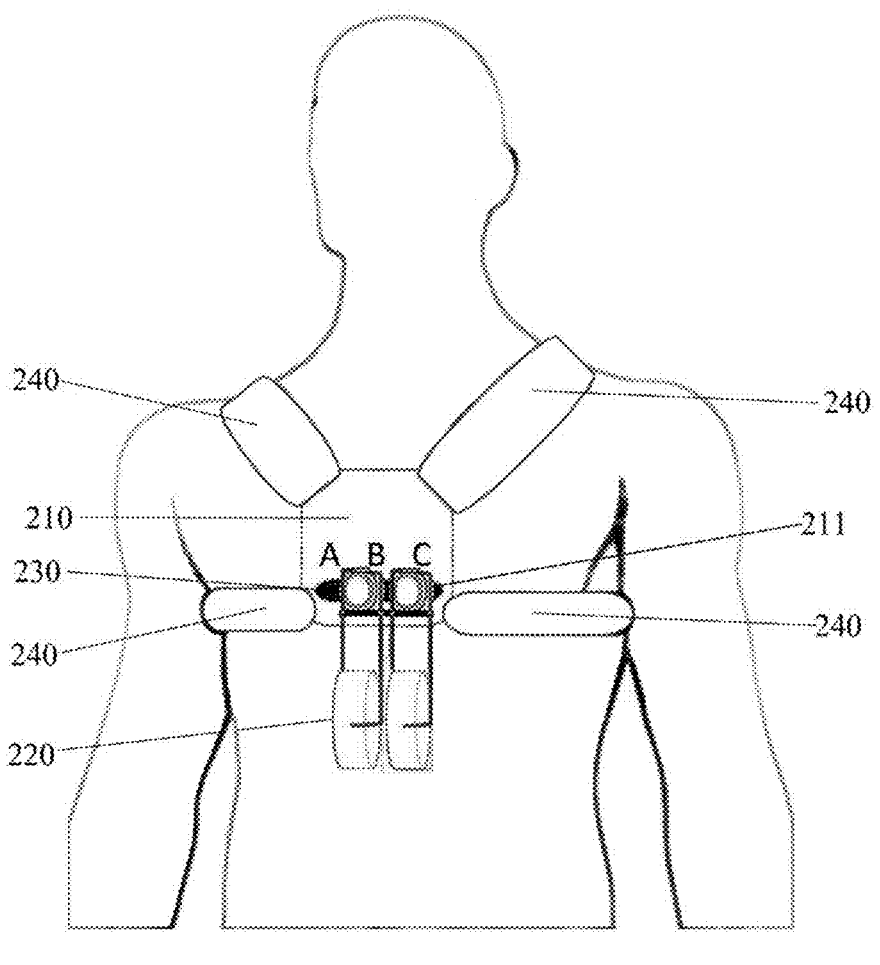
FIG. 7 is a schematic structural diagram of the device for controlling one or more curve angles of scoliosis according to the second embodiment of the present disclosure.

As an example, as shown in FIG. 7, the holding module 210 is provided with a horizontal slot 211; multiple of the weight-hanging sites 230 are provided in the horizontal slot 211, and the plurality of the weight-hanging sites 230 are configured to slide within the horizontal slot 211 to be located at the different suspension positions.

In the above scheme, by providing the horizontal slot 211, multiple of the weight-hanging sites 230 may simply and easily move between the different suspension positions, thereby achieving the purpose of adjusting the number and the center of gravity of the weight module 220.

In some embodiments, the holding module 210 further includes a restricting portion (not shown), and the restricting portion is used to restrict the weight-hanging site 230 after the position of the weight-hanging site 230 has been determined, preventing the weight-hanging site 230 from shifting, which results in loss or reduction of correction effects.

Alternatively, multiple restricting slots are provided at a lower edge of the horizontal slot 211, and multiple of the weight-hanging sites 230 are embedded in the restricting slots, thereby preventing the weight-hanging sites 230 from shifting.

The weight-hanging site 230 in the above embodiment may be in the form of a hook, a hanging rod, etc., or other forms capable of realizing the above function, which is not limited in the present disclosure.

In some embodiments, the holding module 210 may also be provided with a platform. The platform is configured to place a device such as a gradient meter or a smartphone to thereby determine whether the horizontal slot 211 is at a horizontal position after the holding module 210 has been worn at the front-of-chest position of the user.

Alternatively, the platform and the holding module 210 are in the form of a removable or collapsible attachment.

All other technical features of the present embodiment may be referred to the relevant features in the device 100 for controlling one or more curve angles of scoliosis as shown in FIG. 1 to FIG. 5, detailed description thereof will be omitted herein in the present disclosure.

In addition, the present disclosure further provides another form of device for controlling one or more curve angles of scoliosis. The device for controlling one or more curve angles of scoliosis includes a front chest bag and a weight-bearing module. The front chest bag is configured to be worn at a front-of-chest position of a user. The weight-bearing module is fixedly disposed in the front chest bag, the weight-bearing module is configured to carry an article, and a weight of the carried article is configured to keep one or more curve angles of scoliosis of the user within a pre-defined range. In the above scheme, by configuring the device for controlling one or more curve angles of scoliosis in a form similar to a schoolbag, it is convenient to be worn by adolescent and child users to control the one or more curve angles of scoliosis of the user.

The Foregoing Embodiment of the Present Disclosure Will be Described in Detail Below in Conjunction with FIG. 8 and FIG. 9.

Figure 8:
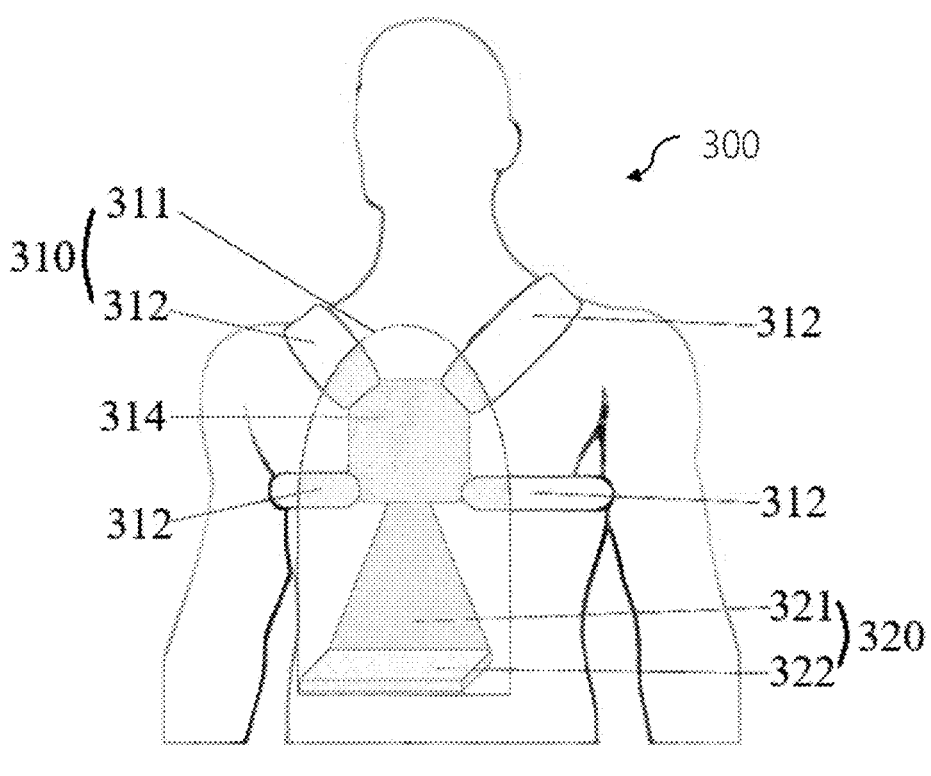
FIG. 8 is a front view of a user after wearing a device for controlling one or more curve angles of scoliosis according to a third embodiment of the present disclosure.

FIG. 8 shows a schematic structural diagram of an apparatus 300 for controlling one or more curve angles according to an embodiment of the present disclosure. In the embodiment as shown in FIG. 8, the apparatus 300 for controlling one or more curve angles includes a front chest pouch bag 310 and a weight-bearing unit 320.

In some embodiments, the front chest bag 310 includes a main pouch 311, shoulder straps 312, and a back connecting strap 313 connecting the two shoulder straps 312, where the main pouch component may be a bag-like object, such as a school bag. The main pouch 311 has two shoulder straps 312 attached thereto for wearing the front chest bag at the front-of-chest position of the user. The back connecting strap 313 is also connected between the two shoulder straps 312. When the front chest bag is worn on the user, the back connecting strap 313 is located at a back position of the user, e.g., an upper vertebrae position, as shown with reference to FIG. 9.

The aforementioned weight-bearing unit is now represented by a weight-bearing unit 320 of this front chest bag, which is fixedly disposed in the main pouch component 311, the weight-bearing unit 320 is intended to carry articles, and the weight of the carried articles is configured to keep the one or more curve angles of scoliosis of the user within the pre-defined range. The weight is obtained by the aforementioned method of implementation. The carried articles weight may be 50-100% of the weight during testing.

In some embodiments, as shown in FIG. 8, the weight-bearing unit 320 may, for example, include a connecting frame 321 and a weight-bearing platform 322. The connecting frame 321 extends in the direction of weight and is configured to be fixedly connected to one side of an interior of the main pouch 311 that is close to the front-of-chest position of the user. As an example, the side of the interior of the main pouch 311 that is close to the front-of-chest position of the user may also be provided with a mounting unit 314, for fixation of the connecting frame 321. The weight-bearing platform 322 is connected to the connecting frame 321, and the weight-bearing platform 322 extends in a horizontal direction. The weight-bearing platform 322 may be used as a weight bearing platform for carrying articles, such as for carrying books for children and adolescents.

Alternatively, the connecting frame 321 and the weight-bearing platform 322 are located at a position directly in the middle of the interior of the main pouch 311 of the front chest bag.

Figure 9:
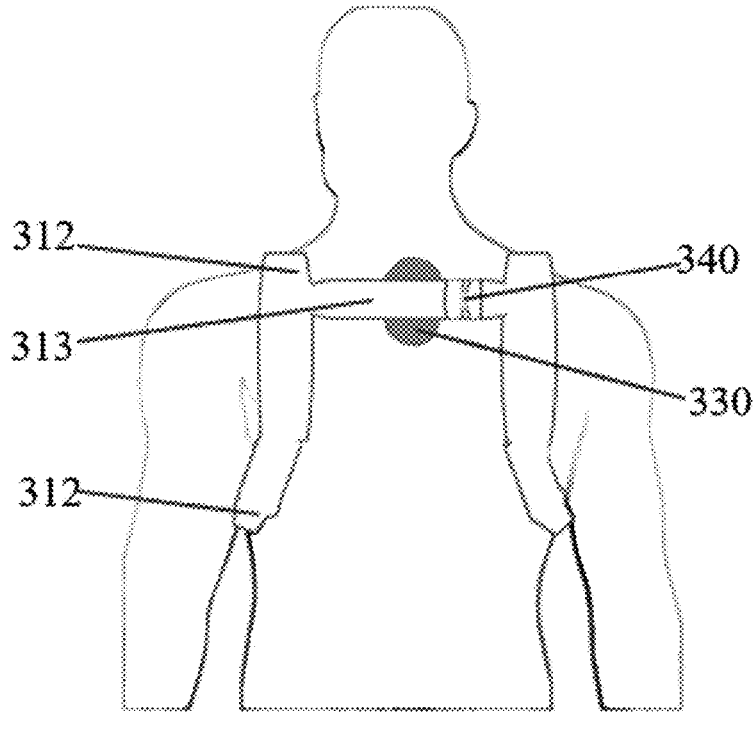
FIG. 9 is a rear view of a user after wearing the device for controlling one or more curve angles of scoliosis according to the third embodiment of the present disclosure.

In some embodiments, as shown in FIG. 9, the back connecting strap 313 may be made of a highly elastic material, and the back connecting strap 313 constitutes the pressure pad of the device for controlling one or more curve angles of scoliosis. When worn, the back connecting strap 313 is positioned at a high thoracic vertebra (e.g., T1 to T6) and above the apex vertebra corresponding to the apex of the scoliotic spine curvature. The highly elastic back connecting strap 313 may also embed a pressure pad 330 at a position in close proximity to the vertebrae, so that the pressure provided by the back connecting strap 313 is evenly distributed across the vertebrae, to push vertebrae forward from the back of the user, therefore the force of pushing the thoracic vertebrae forward is increased, which is helpful in controlling the one or more curve angles of scoliosis of the user.

In some embodiments, the back connecting strap 313 may also be equipped with a simple buckle 340 that facilitates opening and locking the back connecting strap 313.

In addition, the present disclosure further provides a method 400 for using the device for controlling one or more curve angles of scoliosis, as shown in FIG. 10, including the following steps.

S410, measuring one or more curve (Cobb) angles of scoliosis of a non weight-bearing user;

S420, selecting a weight-load for the weight module that keeps the one or more curve angles of scoliosis of the user within a pre-defined range;

S430, wearing the device for controlling one or more curve angles of scoliosis at a front-of-chest position of the user;

S440, re-measuring one or more curve angles of scoliosis of the user after wearing the device for controlling one or more curve angles of scoliosis to confirm that the one or more curve angles (one or more Cobb angles) is reduced; and S450, adjusting the hanging position and/or the weight-load of the weight module to keep the one or more curve angles of scoliosis of the user within the pre-defined range.

In some embodiments, the device for controlling one or more curve angles of scoliosis is used for several hours/day (e.g., during class time). In the above process, the device for controlling one or more curve angles is worn at the front-of-chest position of the user and does not need to interact with other body parts of the user, and the weight-load of the weight module unit alone is used to achieve the purpose of controlling and reducing the one or more curve angles of scoliosis of the user. Moreover, the device for controlling one or more curve angles in the present disclosure does not require the user to use the apparatus 24 hours a day, but only a few hours a day. This design makes the use of the device for controlling one or more curve angles safer and more convenient, while also having more significant and wider effects, and is suitable for use by most patients with scoliosis.

The device for controlling one or more curve angles of scoliosis in the present disclosure has many effects such as good curvature control, and posture optimization for early-stage patients with scoliosis (10-20 degrees), especially for the prevention and control of early scoliosis in adolescents and children. Not only does it ensure better scoliosis control for the user, but is also easier for the user to use, and does not affect other body parts of the user.

When wearing the device for controlling one or more curve angles of scoliosis at the front-of-chest position of the user as described above, the holding module may be first worn at the front-of-chest position, and then the weight module unit may be suspended on the weight-hanging site.

In some embodiments, the method 400 for using further includes the following steps.

S460, tracking periodically to determine the one or more curve angles of scoliosis of the user during use of the device; and adjusting the hanging-site position and/or the weight-load of the weight module based on the one or more curve angles of scoliosis of the user during use, until the one or more curve angles of scoliosis of the user is within a normal range.

For example, when the user first configures the above device for controlling one or more curve angles in the present disclosure, he or she may be re-examined every six months and re-adjust parameters such as the weight-load of the weight module or the hanging-site position based on a result of the re-examination, so as to find an optimal configuration for the current curve angle.

It should be noted that the parameters such as the weight-load of the weight module or the hanging-site position may be adjusted based on an actual structure of the device 100, the device 200 for controlling one or more curve angles of scoliosis provided in the present disclosure, repeated description thereof will be omitted herein in the present disclosure.

Hereinafter, the present disclosure provides reference data to further illustrate effects of using the device for controlling one or more curve angles of scoliosis.

Patient A, who was diagnosed with scoliosis at the age of 12, had a Cobb angle of 20 degrees at the time of diagnosis. The patient was re-examined about twice a year subsequently, at the age of 13 years and 4 months, and at the age of 13 years and 10 months, results of the follow-up examinations are as shown in Table 1.

At follow-up clinic visits, the curve angle of scoliosis of the user A was examined using low-dose X-ray spinal curvature examination (EOS Imaging System) in three scenarios: no weight-bearing, back weight-bearing, and front-of-chest weight-bearing, in which the weight of the weight-bearing was approximately 7.5 kg. From the testing results at the age of 13 years and 10 months, it can be seen that the Cobb angle increased by 3 degrees at back weight-bearing, suggesting that prolonged back weight-bearing may increase the curve angle of scoliosis, which can affect the growth of the bone and lead to more severe scoliosis. In contrary, in Table 1, the testing results at the age of 13 years and 4 months, and at the age of 13 years and 10 months show that the Cobb angle decreased by 13 degrees and 7 degrees respectively when examined with front-of-chest weight-bearing, suggesting that prolonged front-of-chest weight-bearing may reduce the curve angle of scoliosis of the patient with scoliosis. In this regard, the inventor implemented a front-of-chest weight-bearing scheme for Patient A, when Patient A adhered to the use of the device for controlling one or more curve angles of scoliosis in accordance with the above method of the present disclosure, and progression was in each follow-up examination during use, and the results of the follow-up examinations are as shown in Table 2. In order to more clearly compare the curve angle of scoliosis of Patient A after use of the device for controlling one or more curve angles in the present disclosure with the situation before use, the examining results obtained at the age of 13 years and 4 months, and at the age of 13 years and 10 months of the patient in Table 1 are also shown in Table 2.

Figure 11:
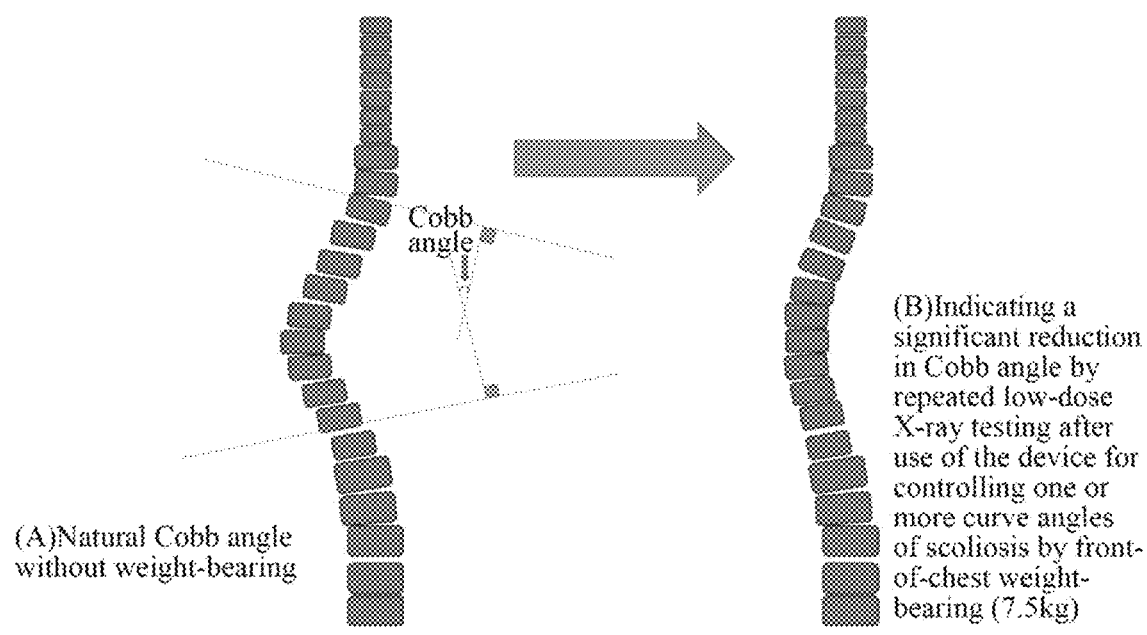
FIG. 11 is a schematic diagram of a method for measuring a Cobb angle and an effect of curvature reduction that may be obtained by repeated spinal imaging after the device for controlling one or more curve angles of scoliosis has been worn by a patient having this immediate effect.

Table 2 records Patient A's body height, natural Cobb angle without weight-bearing, and Cobb angle when front chest weight-bearing (7.5 kg) which were measured using the low-dose X-ray spinal curvature examination at the ages of 13 years and 4 months, 13 years and 10 months, 14 years and 6 months, 15 years old, and 16 years old. For example, in FIG. 11, it shows a trend toward a significant reduction in Cobb angle by repeated X-ray testing over several years after use of this device for controlling one or more curve angles of scoliosis. The results indicate that in three of the five comparisons (13 years and 4 months, 13 years and 10 months, and 15 years old), front chest weight-bearing can significantly reduce the Cobb angle with a probability of 60%. Moreover, the reduction in Cobb angle ranged from 6 to 13 degrees. It can be seen that the curve angle of scoliosis (Cobb angle) can be reduced by front-of-chest weight-bearing most of the time, even at different ages and body heights. In addition, as can be seen from the results of Patient A's use of the device for controlling one or more curve angles in the present disclosure, Patient A's curve angle of scoliosis without weight bearing was reduced from 14 degrees at the age of 13 years and 10 months to 9 degrees at the age of 14 years and 6 months, which has been substantially corrected to be within the normal range. Moreover, by the age of 16 years old when the skeleton is more mature, the curve angle of scoliosis is also maintained at only 9 degrees (which has been restored to the normal range). It can be seen that the device for controlling one or more curve angles of scoliosis in the present disclosure maintained Patient A's curve angle of scoliosis well, as evidenced by the fact that front-of-chest weight-bearing does not exacerbate the curve angle of scoliosis.

In addition, the results in Table 2 also indicate that a curve angle control effect is best at the early stage of the disease (start using at the age of 13 years old) and that the effect is more pronounced when the Cobb angle is between 10-20 degrees. However, the results also show that at a Cobb angle of less than 10 degrees (at the ages of 14 years and 6 months, and 16 years old), the device in the present disclosure did not have an effect of reducing the Cobb angle, therefore, the present device may not be suitable for the case that Cobb angle is less than 10 degrees, because a Cobb angle lower than 10 degrees is already within the normal range and does not require improvement by the present device.

TABLE 1

| Age at which spinal curvature testing is performed | No weight-bearing, Cobb angle | Back weight-bearing, Cobb angle | Front-of-chest weight-bearing, Cobb angle | Conclusion (back weight-bearing exacerbates Cobb angle) |
|---|---|---|---|---|
| 13 years and 4 months | 18 degrees | 13 degrees | 5 degrees | No |
| 13 years and 10 months | 14 degrees | 17 degrees | 7 degrees | Yes |

TABLE 2

| Age at which spinal curvature testing is performed | Body height (cm) | No weight-bearing, Cobb angle | Front-of-chest weight-bearing, Cobb angle | Conclusion (chest weight-bearing can reduce Cobb angle) |
|---|---|---|---|---|
| 13 years and 4 months | 156 | 18 degrees | 5 degrees | Yes |
| 13 years and 10 months | 161 | 14 degrees | 7 degrees | Yes |
| 14 years and 6 months | 165 | 9 degrees | 11 degrees | No |
| 15 years old | 166 | 10 degrees | 4 degrees | Yes |
| 16 years old | 170 | 9 degrees | 10 degrees | No |

CITATIONS

[1]. Centers for Disease Control "<Technical Guidelines for Prevention and Control of Spinal Curvature Abnor-
malities in Children and Adolescents> and Compiling Instructions." Jan. 11, 2021.

[2]. http://www.nhc.gov.cn/jkj/s5899tg/202111/5579c1240d034ac680a7505994aa082d.shtml

[3]. Wenlei Wang, Yifeng Da, Chai Qiang, Yidan Gao, Huang Zhi, Feng Li, Wenkai Zheng, and Yong Zhu. 2021. "Research Progress of Brace and Conservative Treatment of Adolescent Idiopathic Scoliosis." Advances in Clinical Medicine 11 (November): 5477. https://doi.org/10.12677/ACM.2021.1111811.

[4]. Hawary, Ron El, Daphna Zaaroor-Regev, Yizhar Floman, Baron S. Lonner, Yasser Ibrahim Alkhalife, and Randal R. Betz. 2019. "Brace Treatment in Adolescent Idiopathic Scoliosis: Risk Factors for Failure—a Literature Review." The Spine Journal 19 (12): 1917-25. https://doi.org/10.1016/j.spinee.2019.07.008.

[5]. Negrini S, Donzelli S, Aulisa A G, Czaprowski D, Schreiber S, de Mauroy J C, Diers H, Grivas T B, Knott P. Kotwicki T, Lebel A, Marti C, Maruyama T, O'Brien J, Price N, Parent E, Rigo M, Romano M, Stikeleather L. Wynne J, Zaina F. 2016 SOSORT guidelines: orthopaedic and rehabilitation treatment of idiopathic scoliosis during growth. Scoliosis Spinal Disord. 2018 Jan. 10; 13:3. doi: 10.1186/s13013-017-0145-8. PMID: 29435499; PMCID: PMC5795289.

[6]. Negrini, Stefano, Angelo Gabriele Aulisa, Pavel Cerny, Jean Claude de Mauroy, Jeb McAviney, Andrew Mills, Sabrina Donzelli, et al. 2022. "The Classification of Scoliosis Braces Developed by SOSORT with SRS, ISPO, and POSNA and Approved by ESPRM." European Spine Journal 31 (4): 980-89. https://doi.org/10.1007/s00586-022-07131-z.

[7]. ZOU Yi-ming, ZHAO Jian, BAI Jin-yi, YANG Chang-wei, KANG Yi-fan. Biomechanical characteristics and therapy strategy of idiopathic scoliosis: research advances[J]. Academic Journal of Second Military Medical University, 2019, 40(4): 356-361.

[8]. Cheng, Jack C., René M. Castelein, Winnie C. Chu, Aina J. Danielsson, Matthew B. Dobbs, Theodoros B. Grivas, Christina A. Gurnett, et al. 2015. "Adolescent Idiopathic Scoliosis." Nature Reviews Disease Primers 1 (October): nrdp201568. https://doi.org/10.1038/nrdp.2015.68.

[9]. Weinstein, Stuart L., Lori A. Dolan, Jack C. Y. Cheng, Aina Danielsson, and Jose A. Morcuende. 2008. "Adolescent Idiopathic Scoliosis." Lancet (London, England) 371 (9623): 1527-37. https://doi.org/10.1016/S0140-6736(08)60658-3.

[10]. Weinstein, Stuart L., Lori A. Dolan, James G. Wright, and Matthew B. Dobbs. 2013. "Effects of Bracing in Adolescents with Idiopathic Scoliosis." The New England Journal of Medicine 369 (16): 1512-21. https://doi.org/10.1056/NEJMoa1307337.

[11]. Wong, Man Sang, Jack C. Y. Cheng, Tsz Ping Lam, Bobby K. W. Ng, Sai Wing Sin, Sandra L. F. Lee-Shum, [14]. Daniel H. K. Chow, and Sandra Y. P. Tam. 2008. "The Effect of Rigid versus Flexible Spinal Orthosis on the Clinical Efficacy and Acceptance of the Patients with Adolescent Idiopathic Scoliosis." Spine 33 (12): 1360-65. https://doi.org/10.1097/BRS.0b013e31817329d9.

[12]. Desaute, Pascal. 2017. Radiographic imaging device and detector for a radiographic imaging device. United States U.S. Pat. No. 9,535,168B2, filed May 6, 2010, and issued Jan. 3, 2017.

[13]. Zheng, Yongping, and James Chung Wai Cheung. 2014. Three-dimensional (3D) ultrasound imaging system for assessing scoliosis. United States U.S. Pat. No. 8,900,146B2, filed Jul. 27, 2009, and issued Dec. 2, 2014.

The above description is only embodiments of the present disclosure and an illustration of the technical principles utilized. It should be understood by those skilled in the art that the scope of protection involved in the present disclosure is not limited to the technical solution resulting from a specific combination of the above technical features, but also covers other technical solutions formed by any combination of the above technical features or their equivalent features without departing from the technical concept. For example, technical solutions formed by replacing the above features with technical features disclosed in the present disclosure but not limited to those having similar functions.

What is claimed is:

1. A device for controlling one or more curve angles of scoliosis, comprising:

a holding module, configured to be worn at a front-of-chest position of a user, the holding module being provided with a weight-hanging site; and a weight module, suspended on or connected to the weight-hanging site so as to hang below the holding module, a weight-load of the weight module being configured to keep one or more curve angles of scoliosis of the user within a pre-defined range; and wherein the weight-hanging site is configured to select among a plurality of different hanging positions to suspend the weight module thereon; and when the weight-hanging site is at different hanging positions, the weight-load of the weight module suspended on the weight-hanging site is configured to keep the one or more curve angles of scoliosis of the user within the pre-defined range; and wherein the holding module is provided with a horizontal slot, the weight-hanging site is provided in the horizontal slot, and the weight-hanging site is configured to slide within the horizontal slot to move between the plurality of different hanging positions for locations of different hanging positions.

2. The device for controlling one or more curve angles of scoliosis according to claim 1, wherein the holding module is provided with a plurality of weight-hanging sites, the plurality of weight-hanging sites are located at different hanging positions; and when the plurality of the weight-hanging sites in different combinations suspend the weight module, a combination of weight-loads of the weight module keeps the one or more curve angles of scoliosis of the user within the pre-defined range.

3. The device for controlling one or more curve angles of scoliosis according to claim 2, wherein the plurality of weight-hanging sites in different combinations are located on a same horizontal line.

4. The device for controlling one or more curve angles of scoliosis according to claim 3, further comprising:

shoulder straps, connected to the holding module, used to position the holding module at the front-of-chest position of the user when worn on shoulders of the user; and a pressure pad, provided on a back connecting strap between the shoulder straps, being configured to be located at a back position opposite the front-of-chest position, wherein the pressure pad is configured to press vertebrae forward from the back.

5. The device for controlling one or more curve angles of scoliosis according to claim 2, further comprising:

shoulder straps, connected to the holding module, used to position the holding module at the front-of-chest position of the user when worn on shoulders of the user; and a pressure pad, provided on a back connecting strap between the shoulder straps, being configured to be located at a back position opposite the front-of-chest position, wherein the pressure pad is configured to press vertebrae forward from the back.

6. The device for controlling one or more curve angles of scoliosis according to claim 1, further comprising:

shoulder straps, connected to the holding module, used to position the holding module at the front-of-chest position of the user when worn on shoulders of the user; and a pressure pad, provided on a back connecting strap between the shoulder straps, being configured to be located at a back position opposite the front-of-chest position, wherein the pressure pad is configured to press vertebrae forward from the back.

7. The device for controlling one or more curve angles of scoliosis according to claim 6, further comprising:

a pouch bag, the pouch bag having a holding space;

wherein the holding module and the weight module are provided in the holding space of the pouch bag, and the shoulder straps are connected to the pouch bag.

8. A method for using the device for controlling one or more curve angles of scoliosis according to claim 1, wherein the method comprises:

determining the one or more curve angles of scoliosis of the user;

determining the weight-load for the weight module that keeps the one or more curve angles of scoliosis of the user within the pre-defined range;

wearing the device at the front-of-chest position of the user;

re-determining the one or more curve angles of scoliosis of the user after wearing the device; and adjusting a hanging position of the plurality of different hanging positions and/or the weight-load of the weight module to keep the one or more curve angles of scoliosis of the user within the pre-defined range.

9. The method according to claim 8, wherein the method further comprises:

tracking periodically to determine the one or more curve angles of scoliosis of the user during use of the device; and adjusting the hanging position and/or the weight-load of the weight module based on the one or more curve angles of scoliosis of the user determined during the use, until the one or more curve angles of scoliosis of the user is within the pre-defined range.

10. The method according to claim 8, wherein a duration of using the device is several hours per day.

11. The device for controlling one or more curve angles of scoliosis according to claim 1, wherein the holding module, the weight-hanging site and the weight module are made of a material transparent to X-rays.

* * * * *